US007910355B2

(12) United States Patent
Tsuchiya et al.

(10) Patent No.: US 7,910,355 B2
(45) Date of Patent: Mar. 22, 2011

(54) CULTURE OBSERVATION APPARATUS

(75) Inventors: Atsuhiro Tsuchiya, Tokyo (JP); Ryuichi Hirano, Tokyo (JP); Hideaki Endo, Tokyo (JP); Kenichi Koyama, Tokyo (JP); Kazuhiro Hasegawa, Tokyo (JP); Akitsugu Kagayama, Tokyo (JP); Katsuyoshi Yamaguchi, Tokyo (JP)

(73) Assignee: Olympus Corporation, Tokyo (JP)

( * ) Notice: Subject to any disclaimer, the term of this patent is extended or adjusted under 35 U.S.C. 154(b) by 1473 days.

(21) Appl. No.: 11/318,416

(22) Filed: Dec. 22, 2005

(65) Prior Publication Data

US 2006/0141613 A1   Jun. 29, 2006

(30) Foreign Application Priority Data

Dec. 28, 2004   (JP) .................................. 2004-381521

(51) Int. Cl.
  C12M 1/34    (2006.01)
  C12M 3/00    (2006.01)
  G02B 21/26   (2006.01)
  G02B 21/34   (2006.01)
  G01N 21/01   (2006.01)

(52) U.S. Cl. .................. 435/288.7; 435/303.1; 359/395; 359/398

(58) Field of Classification Search ............... 435/288.7, 435/303.1, 809; 359/820, 809, 387, 395, 359/398, 656, 661, 811, 819
See application file for complete search history.

(56) References Cited

U.S. PATENT DOCUMENTS

| | | | | | |
|---|---|---|---|---|---|
| 832,219 | A | * | 10/1906 | Spear | ............................ 114/340 |
| 4,090,921 | A | * | 5/1978 | Sawamura et al. | ......... 435/286.2 |
| 4,629,862 | A | * | 12/1986 | Kitagawa et al. | ............. 219/200 |
| 5,859,727 | A | * | 1/1999 | Tsuchiya | ........................ 359/387 |
| 6,170,167 | B1 | * | 1/2001 | Kato | ................................ 34/80 |
| 2001/0028443 | A1 | | 10/2001 | Yabu | |
| 2005/0105172 | A1 | * | 5/2005 | Hasegawa et al. | ............ 359/368 |
| 2005/0248836 | A1 | | 11/2005 | Tsuchiya | |

FOREIGN PATENT DOCUMENTS

| | | |
|---|---|---|
| EP | 1 548 484 A1 | 6/2005 |
| EP | 1 553 166 A1 | 7/2005 |
| JP | 3-57744 B2 | 9/1991 |
| JP | 2592712 Y2 | 1/1999 |
| JP | 11-133307 A | 5/1999 |
| JP | 2001-092000 A | 4/2001 |
| JP | 2001-350099 A | 12/2001 |
| WO | WO 2004/021066 A1 | 3/2004 |

* cited by examiner

Primary Examiner — William H Beisner
Assistant Examiner — Danielle Henkel
(74) Attorney, Agent, or Firm — Holtz, Holtz, Goodman & Chick, PC (57) ABSTRACT

A culture observation apparatus, which is used for observing a cultured cell while culturing the cell, includes a culture device that cultures the cultured cell, and a microscope used for observing the cultured cell. The culture device includes a first space that is controlled to an environment suitable for culture of the cell, and a second space that is controlled to a lower humidity condition in comparison with the first space. The microscope includes an objective optical unit including an objective lens; the objective optical unit having at least one portion located in the second space, and another portion extending into the first space through an opening formed in a partition wall that separates the first space and the second space, with a gap between the objective optical unit and the partition wall being sealed by a sealing member, and the objective lens includes a plurality of lens groups, with mutual spaces among the lens groups vented to the second space.

18 Claims, 9 Drawing Sheets

CULTURE OBSERVATION APPARATUS

CROSS-REFERENCE TO RELATED APPLICATIONS

This application is based upon and claims the benefit of priority from Japanese Patent Application No. 2004-381521, filed on Dec. 28, 2004, the entire contents of which are incorporated herein by reference.

BACKGROUND OF THE INVENTION

1. Field of the Invention

This invention relates to a culture observation apparatus that is used for observing cultured cells while culturing the cells.

2. Description of the Related Art

In the field of biological research, various experiments have been conducted with the use of cultured cells for the study of dynamic changes in living organisms. The cultured cells are placed in a carbon dioxide incubator that is kept at an inner temperature of 37° C., a carbon dioxide gas concentration of 5%, and a humidity of 100%, together with a liquid referred to as a culture medium made from bovine-serum or the like, so that the activities of the cultured cells are maintained. Moreover, observation apparatuses, which allow observation while the activities of the cultured cells are maintained with the use of a microscope equipped with functions of the carbon dioxide incubator, have been commercially available.

In such an observation apparatus, the tip portion of an objective lens of a microscope is located inside the carbon dioxide incubator, and exposed to a highly humid environment. For this reason, moisture enters the inside of the objective lens, and tends to cause dew condensation on the surface of a lens inside the objective lens. The dew condensation inside the objective lens causes degradation in observed images.

SUMMARY OF THE INVENTION

A culture observation apparatus, which is used for observing a cultured cell while culturing the cell, according to one aspect of the present invention includes a culture device that cultures the cultured cell, and includes a first space that is controlled to an environment suitable for culture of the cell, and a second space that is controlled to a lower humidity condition in comparison with the first space, and a microscope used for observing the cultured cell, and includes an objective optical unit including an objective lens; the objective optical unit having at least one portion located in the second space, and another portion extending into the first space through an opening formed in a partition wall that separates the first space and the second space, with a gap between the objective optical unit and the partition wall being sealed by a sealing member, and the objective lens including a plurality of lens groups, with mutual spaces among the lens groups vented to the second space.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Embodiments of the present invention will be described in detail below with reference to the accompanying drawings.

Figure 1:
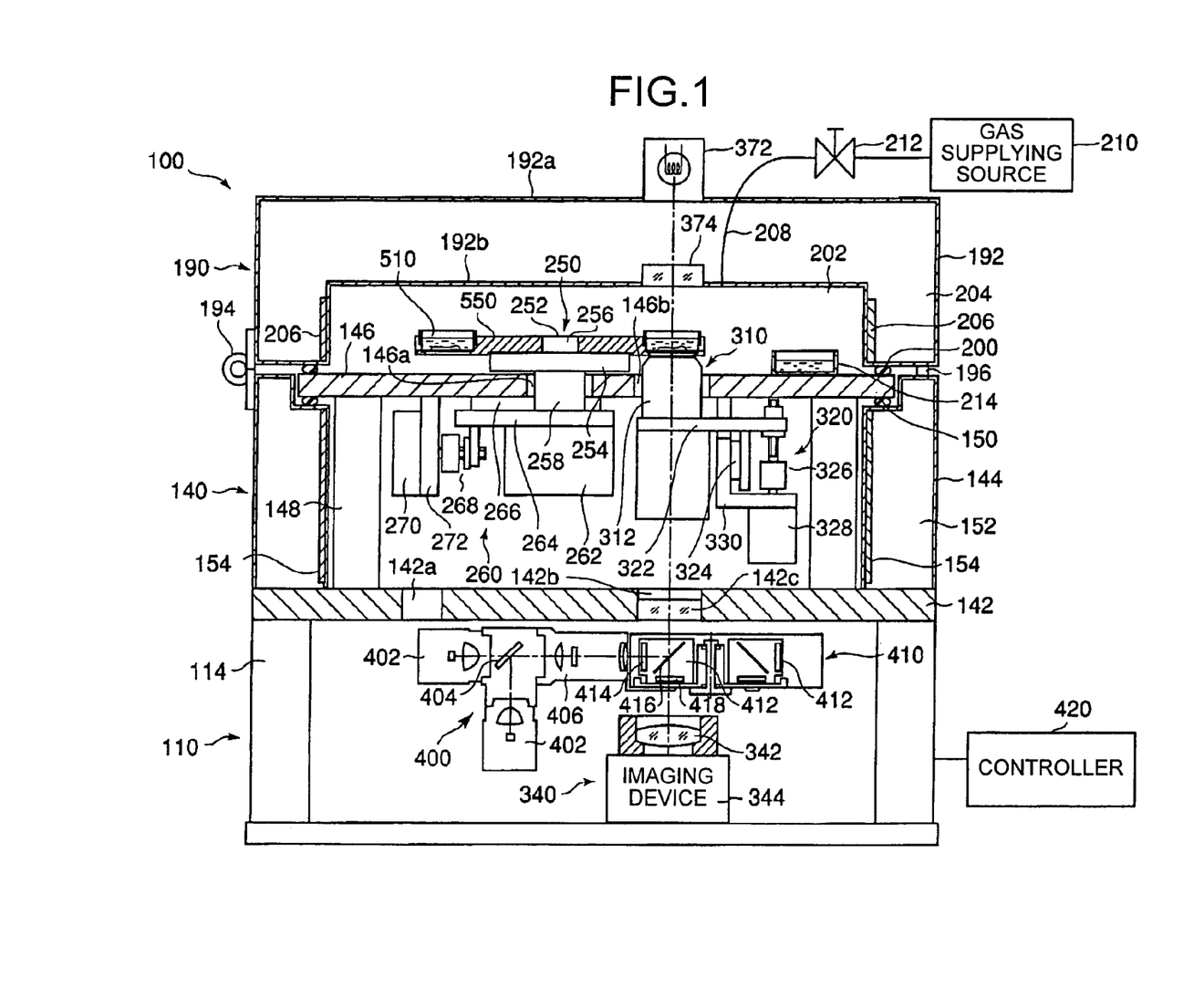
FIG. 1 is a sectional view that schematically shows a culture observation apparatus in accordance with a first embodiment of the present invention.

A first embodiment is directed to a culture observation apparatus for observing a cultured cell while culturing the cell. The culture observation apparatus basically includes a culture device (incubator) used for culturing the cultured cell and a microscope used for observing the cultured cell, which are combined with each other. FIG. 1 is a schematic sectional view of a culture observation apparatus according to the first embodiment of the present invention.

As shown in FIG. 1, the culture observation apparatus 100 includes a culture device main body 190, a culture device sub-main body 140, and a main-body supporting base 110 that supports these.

The main-body supporting base 110 has a plurality of leg members 114.

The culture device sub-main body 140 is provided with a lower base portion 142 that is supported by the leg members 114, a side wall 144 that surrounds the upper periphery of the lower base portion 142, and an upper base portion 146 that covers an opening on the upper side of the side wall 144.

The upper base portion 146 is supported by a plurality of supporting pillars 148 that stand on the lower base portion 142. The upper base portion 146 and the side wall 144 are made in contact with each other through a seal member 150, with a gap between these being kept in an air-tight state. The side wall 144 has a hollow structure including a heat-insulating space 152, and a heater 154 is installed inside the heat-insulating space 152 of the side wall 144. The lower base portion 142 has a through hole 142a having a diameter of about 30 mm, which allows the inner space of the culture device sub-main body 140 to communicate with outside air.

The culture device main body 190 is provided with a box-shaped case member 192 with an opening on the bottom face. The case member 192 is attached to the side wall 144 by hinges 194 so as to be opened and closed with respect to the culture device sub-main body 140. A seal member 200 is placed between the case member 192 and the upper base portion 146, and when closed, the case member 192 is made in contact with the upper base portion 146 through the seal member 200, with a gap between the case member 192 and the upper base portion 146 being kept in an air-tight state. The case member 192 has a hollow structure including a heat-insulating space 204, and a heater 206 is installed inside the heat-insulating space 204 of the case member 192.

When the case member 192 is closed, the culture device sub-main body 140 and the culture device main body 190 are allowed to form a culture space 202 used for culturing a sample. The culture observation apparatus 100 is provided with an open/close sensor 196 for sensing the opening and closing of the case member 192.

A gas supplying flow path 208, used for supplying a gas such as a carbon dioxide gas to the culture space 202, is connected to the case member 192. The gas supplying flow path 208 is connected to a gas supplying source 210, and a valve 212 used for controlling the amount of supply of the gas is installed in the middle of the gas supplying flow path 208.

The culture observation apparatus 100 is provided with a tray attaching unit 252 to which a sample tray 550 is attached and a horizontal shifting mechanism 260 used for shifting the tray attaching unit 252 horizontally inside the culture space 202.

A sample tray 550 is capable of holding a plurality of samples 510. Each sample 510 includes a container 512 housing cultured cells 502 and a culture medium 504, and a lid 518 covering the container 512. Both of the container 512 and the lid 518 are optically transparent. Each sample 510 is placed in a depressed section formed in the sample tray 550 and supported therein, and can be optically observed from below through an opening formed inside the depressed section.

The tray attaching unit 252 has a tray receiving unit 254 that receives the sample tray 550, a protruding portion 256 that protrudes upward from the tray receiving unit 254 and a rotation shaft 258 that extends downward from the tray receiving unit 254. The rotation shaft 258 is rotatably supported by a mechanism not shown.

Although not shown in figures, the sample tray 550 has a grabbing mechanism that grabs the protruding portion 256 of the tray attaching unit 252, and the grabbing mechanism forms a tray holding mechanism in cooperation with the tray attaching unit 252. Thus, the sample tray 550 can be detachably attached to the tray attaching unit 252 with good reproducibility so that the upper face thereof is placed in parallel with a plane that is orthogonal to the light axis of an objective lens 312.

The upper base portion 146 has a through hole 146a, and the rotation shaft 258 of the tray attaching unit 252 extends through the through hole 146a of the upper base portion 146. A gap between the upper face of the upper base portion 146 and the lower face of the tray receiving unit 254 is preferably set to 0.1 mm or less in order to preferably suppress a leak of moisture. Moreover, in order to further suppress the leak of moisture, a seal member may be placed between the upper face of the upper base portion 146 and the lower face of the tray receiving unit 254.

The horizontal shifting mechanism 260 is provided with a motor 262 used for rotating the tray attaching unit 252, a motor supporting member 264 that supports the motor 262, a linear guide 266 that shiftably supports the motor supporting member 264, a ball screw 268 that is engaged with the motor supporting member 264, a motor 270 used for driving the ball screw 268, and a motor supporting member 272 that supports the motor 270.

The motor supporting member 264 is attached to the upper base portion 146 through the linear guide 266, and allowed to shift laterally with respect to the upper base portion 146; Here, the motor supporting member 272 is secured to the upper base portion 146. Moreover, the ball screw 268 converts a rotation movement of the shaft of the motor 270 to a linear movement of the motor supporting member 264.

The microscope is provided with an objective optical unit 310 and an image-forming optical unit 340. The objective optical unit 310 is housed inside the culture device sub-main body 140. The image-forming optical unit 340 is placed on a lower outer portion of the culture device sub-main body 140.

The objective optical unit 310 is provided with an objective lens 312 and a focusing mechanism 320 used for shifting the objective lens 312 upward and downward.

The focusing mechanism 320 is provided with an objective lens supporting member 322 that supports the objective lens 312, a linear guide 324 that shiftably supports the objective lens supporting member 322, a ball screw 326 that is engaged with the objective lens supporting member 322, a motor 328 used for driving the ball screw 326, and a motor supporting member 330 that supports the motor 328.

The motor supporting member 330 is secured to the upper base portion 146. The objective lens supporting member 322, which is attached to the motor supporting member 330 through the linear guide 324, is capable of shifting upward and downward with respect to the motor supporting member 330. The ball screw 326 converts a rotation movement of the shaft of the motor 328 to a linear movement of the objective lens supporting member 322.

The upper base portion 146 has a through hole 146b, and the objective lens 312 extends through the through hole 146b of the upper base portion 146. A gap between the through hole 146b of the upper base portion 146 and the objective lens 312 is preferably set to 0.1 mm or less in order to preferably suppress a leak of moisture. Moreover, in order to further suppress the leak of moisture, a seal member may be placed between the through hole 146b of the upper base portion 146 and the objective lens 312.

The image-forming optical unit 340 is provided with an image-forming lens 342 and an imaging device 344. The lower base portion 142 has a through hole 142b, and an optical window 142c is formed in the through hole 142b in a tightly-sealed state. The image-forming optical unit 340 is optically coupled to the objective lens 312 through the optical window 142c formed in the lower base portion 142.

Moreover, the microscope is provided with a transmissive lighting optical system used for providing transmissive lighting of the sample 510. The transmissive lighting optical system is provided with an illuminating light source 372 that is attached to an outer wall 192a of the case member 192 in a tightly-sealed state, and an optical window 374 that is formed in an inner wall 192b of the case member 192 in a tightly-sealed state. Both of the illuminating light source 372 and the optical window 374 are located above the objective lens 312.

The illuminating light source 372 emits illuminating light, and the optical window 374 allows the illuminating light to pass therethrough.

Moreover, the microscope is provided with an excitation lighting optical system used for exciting the sample. This excitation lighting optical system has an exciting light source 400 and a fluorescent cube unit 410.

The exciting light source 400 includes a plurality of exciting light sources 402, and these emit light rays having different wavelengths. The exciting light source 400 further includes an element 404 that unifies light paths extending from the exciting light sources 402 into one path and a projection tube 406 that directs light rays from the element 404 to the fluorescent cube unit 410.

The fluorescent cube unit 410 includes a plurality of fluorescent cubes 412. The fluorescent cubes 412 are held, for example, in a rotatable turret, and one of the fluorescent cubes 412 is selectively positioned on a light path between the objective optical unit 310 and the image-forming optical unit 340. Each of the fluorescent cubes 412 is provided with a fluorescent filter 414, a dichroic mirror 416, and an absorbing filter 418. The fluorescent filter 414 selectively transmits light rays having specific wavelengths to generate an excited light ray. The dichroic mirror 416 reflects the excited light ray that has been transmitted through the fluorescent filter 414, and also selectively transmits fluorescent light generated from the sample 510. The absorbing filter 418 selectively transmits light rays having specific wavelength ranges in the fluorescent light that has been transmitted through the dichroic mirror 416 so that undesired wavelength components are removed therefrom.

The culture observation apparatus 100 is further provided with a control unit 420 that controls the entire apparatus. The control unit 420 controls, for example, the horizontal shifting mechanism 260, the focusing mechanism 320, the heater 154, the heater 206, the fluorescent cube units 410, the exciting light source 402, and the illuminating light source 372.

Upon using the culture observation apparatus 100, the sample tray 550 holding a plurality of samples 510 is attached to the tray attaching unit 252, and a humidifying pad 214 containing pure water is placed in the culture space 202. The culture space 202 is controlled to 37° C. in its inside temperature by the heater 206, and also to 5% in its carbon dioxide concentration by the valve 212. The inner space of the culture device sub-main body 140 is controlled to 37° C. in its inside temperature by the heater 154.

Since the culture space 202 is hardly influenced by the outside air by the heat-insulating space 204 of the case member 192, and since the inner space of the culture device sub-main body 140 is kept at 37° C., the inner temperature of the culture space 202 is favorably maintained at 37° C. Moreover, since the moisture generated in the culture space 202 is hardly leaked outside, the inside of the culture space 202 is maintained at a high moisture state close to 100%.

Since the through hole 142a that connects the inner space of the culture device sub-main body 140 to the outside space has a small diameter, only a little outside air is allowed to flow into the culture device sub-main body 140. Moreover, since the inner space of the culture device sub-main body 140 is enclosed by the heat-insulating space 152, it is hardly influenced by the outside air. For this reason, the objective lens 312 and the focusing mechanism 320, placed inside the culture device sub-main body 140, are desirably maintained at 37° C. without being influenced by the outside air. When the objective lens 312 and the focusing mechanism 320 are influenced by temperatures, defocusing tends to occur easily; however, since this structure maintains the temperature of the objective lens 312 and the focusing mechanism 320 at a constant temperature, it is possible to favorably prevent the occurrence of defocusing.

Even if slight moisture invades inside the culture device sub-main body 140 from the culture space 202, since the moisture is diffused into the outside air through the through hole 142a, the inside of the culture device sub-main body 140 is maintained at a low level of moisture. Consequently, it becomes possible to prevent the objective lens 312 from dew condensation and also to prevent the focusing mechanism 320 from rusting.

Upon observation, the sample 510 located above the objective lens 312 is observed. The sample 510 to be observed can be switched with the substantial rotation of the sample tray 550 by the horizontal shifting mechanism 260. The observation site within the sample 510 is adjusted by the shift of the sample tray 550 along the plane orthogonal to the light axis of the objective lens 312 by the horizontal shifting mechanism 260. This adjustment is achieved through the combination of the rotation and the translational shift of the sample tray 550. The rotation and the translational shift are carried out within a range in which the tip of the objective lens 312, located inside an opening formed inside a depressed portion which supports the sample 510, is kept from contacting the sample tray 550.

Moreover, upon carrying out a long-term observation, an exchange of culture mediums is required. The exchange of culture mediums is carried out with each of the sample trays 550 being removed from the tray attaching unit 252. In other words, during the exchange of culture mediums, the container 512 and the edge portion 519 of the lid 518 are maintained on the sample tray 550, and firmly secured by the container holding mechanism so that no positional deviations occur. After the exchange of culture mediums, the sample tray 550 is attached again to the tray attaching unit 252 in the same state as the state before the exchange of culture mediums.

In this manner, the culture observation apparatus 100 makes it possible to exchange culture mediums without the necessity of removing the container 512 from the sample tray 550 and also to attach the sample tray 550 to the tray attaching unit 252 with good positional reproducibility; therefore, the container 512 is properly placed at the original position. Thus, it becomes possible to observe a specific cell for a long time.

In the culture observation apparatus 100, since the tip of the objective lens 312 is located in the culture space 202, the tip is exposed to high humidity. In general, the lenses inside the objective lens are secured with a bonding agent, and in general, the bonding agent is not completely moisture-resistant, and allows some moisture to permeate. For this reason, moisture inside the culture space 202 tends to enter the inside of the objective lens 312 to cause dew condensation on the surface of each of the lenses inside the objective lens 312.

Therefore, the culture observation apparatus 100 has a mechanism which prevents dew condensation inside the objective lens 312. The following description will discuss this mechanism, while also discussing the mechanical structure of the objective lens 312. The following explanation will be given, with the objective lens being indicated by different reference numerals depending on features of the structures thereof. In other words, any of objective lenses given in the following description can be applied as the objective lens 312 shown in FIG. 1.

Figure 2:
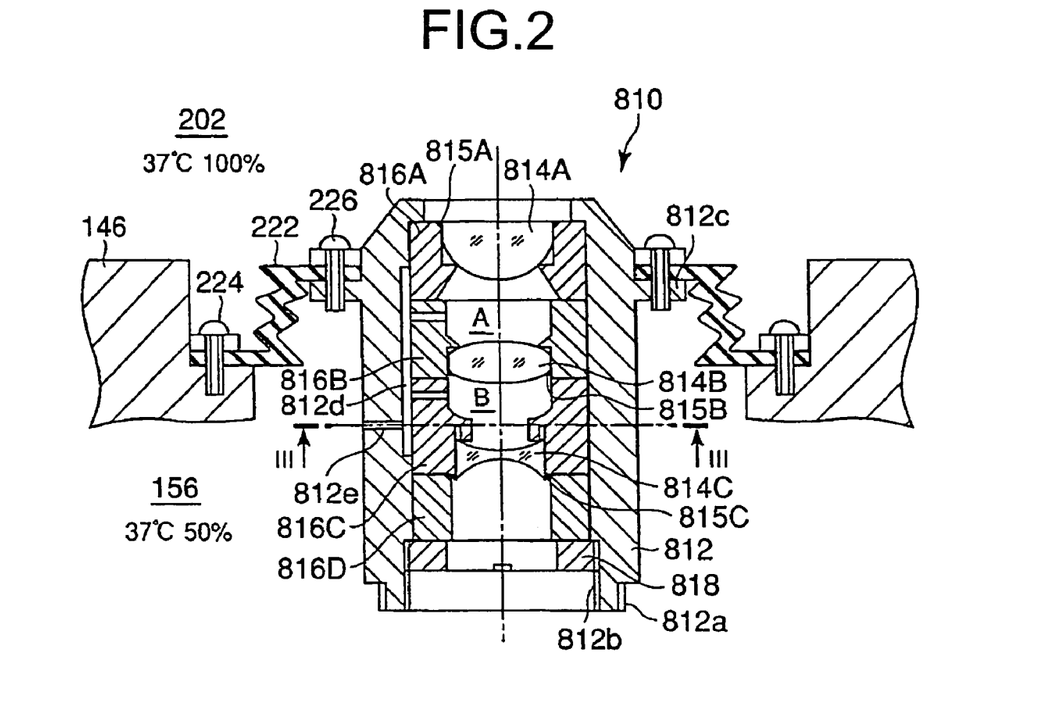
FIG. 2 is a sectional view that shows an objective lens and a peripheral portion thereof in the culture observation apparatus of the first embodiment of the present invention.
Figure 3:
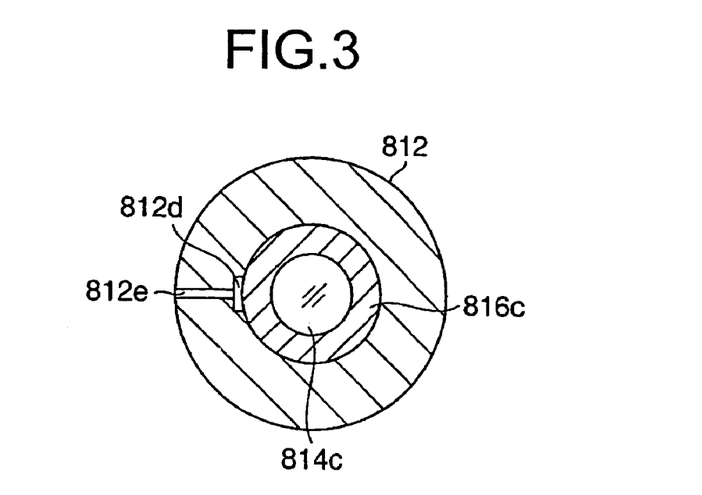
FIG. 3 is a sectional view of the objective lens taken along line III-III of FIG. 2.

FIG. 2 is a sectional view that shows the objective lens and the periphery thereof in the culture observation apparatus in accordance with the first embodiment of the present invention. FIG. 3 is a sectional view of the objective lens taken along line III-III of FIG. 2.

As shown in FIG. 2, an objective lens 810 has such a structure that only its tip is located inside the culture space 202, with the rest being located inside an inner space 156 of the culture device sub-main body 140. As described earlier, the culture space 202 has a high humidity and the inner space 156 of the culture device sub-main body 140 has a lower humidity in comparison with the culture space 202.

The objective lens 810 includes a plurality of lens groups, and is provided with a lens 814A and a lens frame 816A that holds the lens 814A, a lens 814B and a lens frame 816B that holds the lens 814B, and a lens 814C and a lens frame 816C that holds the lens 814C. The respective lenses 814A to 814C and the corresponding lens frames 816A to 816C form one lens group.

The lens 814A is secured to the lens frame 816A with a bonding agent 815A, the lens 814B is secured to the lens frame 816B with a bonding agent 815B, and the lens 814C is secured to the lens frame 816C with a bonding agent 815C.

The objective lens 810 is further provided with an outer cylinder 812 that houses the lens frames 816A to 816C, a hollow frame 816D that is housed in the outer cylinder 812 together with the lens frames 816A to 816C, and a frame securing member 818 used for securing the lens frames 816A to 816C and the hollow frame 816D housed in the outer cylinder 812.

The outer cylinder 812 has a screw portion 812a at its rear end so as to be attached to an objective lens supporting member 322. The outer cylinder 812 has a screw portion 812b on an inner circumferential face near its rear end, with which the frame securing member 818 is engaged.

The outer cylinder 812 has a flange 812c at its tip. A gap between the flange 812c of the outer cylinder 812 and the upper base portion 146 is sealed with a sealing member 222. The sealing member 222 is formed in an accordion shape from an elastic material having a low moisture-permeability such as rubber. The sealing member 222 is secured onto the flange 812c of the outer cylinder 812 by a screw 226 at its inner end portion, with its outer end portion being secured to the upper base portion 146 by a screw 224.

The sealing member 222, which is made in an accordion shape to have an extendable property, virtually does not intervene with longitudinal shifts of the objective lens 810 caused by the focusing mechanism 320. Moreover, the sealing member 222, which is made of the elastic material having low moisture permeability such as rubber, reduces water vapor leak from the culture space 202 to the inner space 156 of the culture device sub-main body 140, making it possible to prevent the inner space 156 of the culture device sub-main body 140 from high humidity.

As shown in FIGS. 2 and 3, the outer cylinder 812 is provided with a groove 812d that extends longitudinally along the inner side face and a through hole 812e that extends in a diameter direction from the groove 812d. Moreover, as shown in FIG. 2, the lens frame 816B and the lens frame 816C respectively have through holes that extend in a diameter direction. Both of the through holes of the lens frame 816B and the lens frame 816C are allowed to communicate with the groove 812d of the outer cylinder 812. Thus, a space A between the lens 814A and the lens 814B is allowed to communicate with the inner space 156 of the culture device sub-main body 140. In the same manner, a space B between the lens 814B and the lens 814C is allowed to communicate with the inner space 156 of the culture device sub-main body 140. Moreover, as described earlier, the inner space 156 of the culture device sub-main body 140 is allowed to communicate with outside air via the through hole 142a of the lower-side base portion 142.

There is a possibility that water vapor inside the culture space 202 enters the space A between the lens 814A and the lens 814B through the bonding agent 815A securing the lens 814A to the lens frame 816A, and further enters the space B between the lens 814B and the lens 814C through the bonding agent 815B securing the lens 814B to the lens frame 816B. However, excessive water vapor inside each of the space A and the space B is allowed to pass through each of the through holes in the lens frame 816A and the lens frame 816B, and directed to the inner space 156 of the culture device sub-main body 140 through each of the groove 812d and the through hole 812e of the outer cylinder 812 to be diffused therein. Moreover, the excessive water vapor inside the inner space 156 of the culture device sub-main body 140 is allowed to pass through the through hole 142a of the lower-side base portion 142 to be diffused in outer air.

With this arrangement, it becomes possible to prevent the excessive water vapor from accumulating in the space A between the lens 814A and the lens 814B as well as in the space B between the lens 814B and the lens 814C to cause high humidity. Thus, it becomes possible to prevent dew condensation on the surface of each of the lens 814A, lens 814B, and lens 814C.

Moreover, since outer air is directed to the space A, the space B, and the inner space 156, it becomes possible to prevent the objective lens from dew condensation without the necessity of preparing the sealing member 222 as a complete sealing material such as metal. Thus, a rubber material or the like, which is an elastic material, although it slightly permeates moisture, may be applied as the sealing member 222. Consequently, this arrangement makes it possible to provide a focusing process with high precision, without preventing the shift of the objective lens from its focusing process.

<Modification of Objective Lens>

Figure 4:
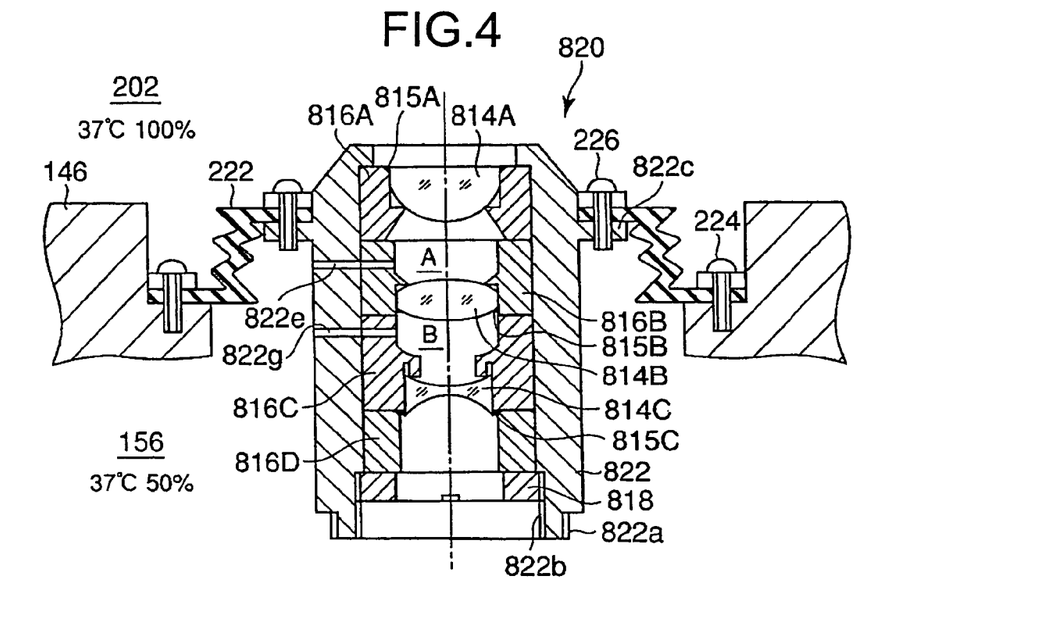
FIG. 4 is a sectional view that shows an objective lens and a peripheral portion thereof in accordance with a modification of the first embodiment of the present invention.

The following description will discuss a modification of the objective lens shown in FIG. 2. FIG. 4 is a sectional view that shows an objective lens and a periphery thereof in accordance with the modification of the first embodiment of the present invention. In FIG. 4, those members that are indicated by the same reference numerals shown in FIG. 2 are the same members, and the detailed description thereof is not repeated.

As shown in FIG. 4, an objective lens 820 has an outer cylinder 822 that houses lens frames 816A to 816C and a hollow frame 816D. The outer cylinder 822 has a screw portion 822a at its rear end so as to be attached to an objective lens supporting member 322, and also has a screw portion 822b on an inner circumferential face near its rear end, with which the frame securing member 818 is engaged. The outer cylinder 822 has a flange 822c at its tip, and a gap between the flange 822c and the upper base portion 146 is sealed with the sealing member 222.

The outer cylinder 822 has a through hole 822e that extends in a diameter direction. The through hole 822e communicates with the through hole of the lens frame 816B. Thus, the space A between the lens 814A and the lens 814B is vented to the inner space 156 of the culture device sub-main body 140 through the through hole of the lens frame 816B and the through hole 822e of the outer cylinder 822.

The outer cylinder 822 also has a through hole 822g that extends in a diameter direction. The through hole 822g communicates with the through hole of the lens frame 816C. Thus, the space B between the lens 814B and the lens 814C is vented to the inner space 156 of the culture device sub-main body 140 through the through hole of the lens frame 816C and the through hole 822g of the outer cylinder 822.

The other structures are the same as those of the objective lens 810 shown in FIG. 2.

The objective lens 820 of the present modification is different from the objective lens 810 only in that the space A between the lens 814A and the lens 814B and the space B between the lens 814B and the lens 814C are independently vented to the inner space 156 of the culture device sub-main body 140, and the other functions and advantages are the same as those of the objective lens 810.

In the present modification, since the through holes 822e and 822g can be machined by a generally-used drill without using a device capable of forming an under-cut shape as required for the groove 812d of the objective lens 810, the objective lens is available more commonly.

In the culture observation apparatus 100 shown in FIG. 1, the case member 192 can be opened and closed with respect to the culture device sub-main body 140; however, not limited to this structure, the case member 192 may be secured to the culture device sub-main body 140. In this case, in order to bring in and take out the sample tray 550 and the humidifying pad 214, the case member 192 is only required to have an opening formed in a side wall and a door used for closing the opening in the side wall. Moreover, the case member 192 may have a structure in which: one portion of the bottom is opened and the opening is closed when attached to the culture device sub-main body 140.

Figure 5:
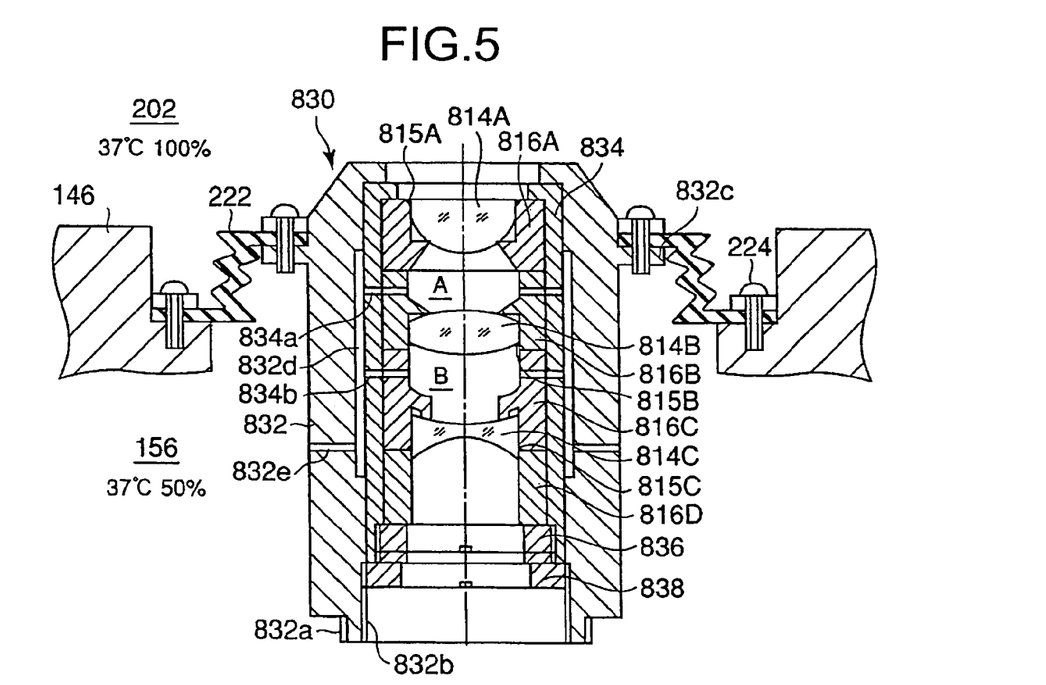
FIG. 5 is a sectional view that shows an objective lens and a peripheral portion thereof in a culture observation apparatus in accordance with a second embodiment of the present invention.

A second embodiment is directed to another objective lens that is used for the culture observation apparatus and is hardly subjected to dew condensation. FIG. 5 is a sectional view that shows an objective lens and a periphery thereof in a culture observation apparatus in accordance with the second embodiment of the present invention. In FIG. 5, those members that are indicated by the same reference numerals shown in FIG. 1 are the same members, and the detailed description thereof is not repeated.

As shown in FIG. 5, an objective lens 830 has an inner cylinder 834 that houses lens frames 816A to 816C and a hollow frame 816D, a frame securing member 836 that secures the lens frames 816A to 816C and the hollow frame 816D housed in the inner cylinder 834, an outer cylinder 832 that houses the inner cylinder 834, and an inner cylinder securing member 838 that secures the inner cylinder 834 housed in the outer cylinder 832.

The outer cylinder 832 has a screw portion 832a at its rear end so as to be attached to an objective lens supporting member 322, and also has a screw portion 832b on an inner circumferential face near its rear end, with which the inner cylinder securing member 838 is engaged. Moreover, the inner cylinder 834 has a screw portion on an inner circumferential face near its rear end, with which the frame securing member 836 is engaged. The outer cylinder 832 has a flange 832c at its tip, and a gap between the flange 832c and the upper base portion 146 is sealed with the sealing member 222.

The lens frame 816B has two through holes that extend in a diameter direction. In the same manner, the lens frame 816C also has two through holes that extend in a diameter direction. The inner cylinder 834 has two through holes 834a that extend in a diameter direction and other two through holes 834b that extend in a diameter direction. The through holes 834a of the inner cylinder 834 communicate with the through holes of the lens frame 816B, and the through holes 834b of the inner cylinder 834 communicate with the through holes of the lens frame 816C. The outer cylinder 832 has a groove 832d that is formed around the inner side face thereof and two through holes 832e that extend from the groove 832d in a diameter direction. The groove 832d communicates with the through holes 834a and the through holes 834b of the inner cylinder 834.

Thus, the space A between the lens 814A and the lens 814B is vented to the inner space 156 of the culture device sub-main body 140 through the through holes of the lens frame 816B, the through holes 834a of the inner cylinder 834, the groove 832d and the through holes 832e of the outer cylinder 832. Moreover, the space B between the lens 814B and the lens 814C is vented to the inner space 156 of the culture device sub-main body 140 through the through holes of the lens frame 816C, the through holes 834b of the inner cylinder 834, the groove 832d and the through holes 832e of the outer cylinder 832.

In this manner, in the objective lens 830 of the second embodiment also, in the same manner as the first embodiment, it becomes possible to prevent excessive water vapor from accumulating in the space A between the lens 814A and the lens 814B as well as in the space B between the lens 814B and the lens 814C to cause high humidity. Thus, it becomes possible to prevent dew condensation on the surface of each of the lens 814A, lens 814B, and lens 814C.

In the second embodiment, since the groove 832d of the outer cylinder 832 is formed along the entire circumference of the inner side face, lathe machining processes are carried out simultaneously together with the other portions of the outer cylinder 832 so that it is possible to carry out the machining process of the outer cylinder 832 comparatively easily.

In the second embodiment, the number of any of the through holes of the lens frame 816B, the through holes of the lens frame 816C, the through holes 834a of the inner cylinder 834, the through holes 834b of the inner cylinder 834, and the through holes 832e of the outer cylinder 832 is set to two; however, not limited to this, the number may be changed as appropriate.

Figure 6:
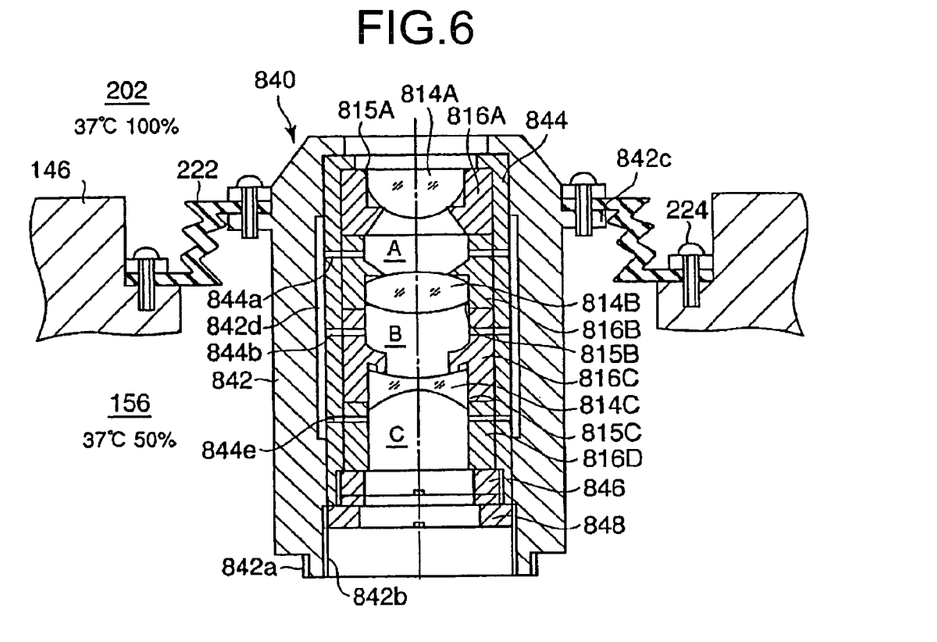
FIG. 6 is a sectional view that shows an objective lens and a peripheral portion thereof in a culture observation apparatus in accordance with a third embodiment of the present invention.

A third embodiment is directed to another objective lens that is used for the culture observation apparatus and is less susceptible to dew condensation. FIG. 6 is a sectional view that shows an objective lens and a periphery thereof in a culture observation apparatus in accordance with the third embodiment of the present invention. In FIG. 6, those members that are indicated by the same reference numerals shown in FIG. 1 are the same members, and the detailed description thereof is not repeated.

As shown in FIG. 6, an objective lens 840 has an inner cylinder 844 that houses lens frames 816A to 816C and a hollow frame 816D, a frame securing member 846 that secures the lens frames 816A to 816C and the hollow frame 816D housed in the inner cylinder 844, an outer cylinder 842 that houses the inner cylinder 844, and an inner cylinder securing member 848 that secures the inner cylinder 844 housed in the outer cylinder 842.

The outer cylinder 842 has a screw portion 842a at its rear end so as to be attached to the objective lens supporting member 322, and also has a screw portion 842b on an inner circumferential face near its rear end, with which the inner cylinder securing member 848 is engaged. Moreover, the inner cylinder 844 has a screw portion on an inner circumferential face near its rear end, with which the frame securing member 846 is engaged. The outer cylinder 842 has a flange 842c at its tip, and a gap between the flange 842c and the upper base portion 146 is sealed with the sealing member 222.

The lens frame 816B has two through holes that extend in a diameter direction. In the same manner, the lens frame 816C has two through holes that extend in a diameter direction. Moreover, the hollow frame 816D also has two through holes that extend in a diameter direction. The inner cylinder 844 has two through holes 844a that extend in a diameter direction, other two through holes 844b that extend in a diameter direction, and the other two through holes 844c that extend in a diameter direction. The through holes 844a of the inner cylinder 844 communicate with the through holes of the lens frame 816B, the through holes 844b of the inner cylinder 844 communicate with the through holes of the lens frame 816C, and the through holes 844c of the inner cylinder 844 communicate with the through holes of the hollow frame 816D. The outer cylinder 842 has a groove 842d that is formed along the inner side face thereof. The groove 842d communicates with the through holes 844a, the through holes 844b, and the through holes 844c of the inner cylinder 844.

Thus, the space A between the lens 814A and the lens 814B is connected to the space C inside the hollow frame 816D through the through holes of the lens frame 816B, the through holes 844a of the inner cylinder 844, the groove 842d of the outer cylinder 842, and the through holes of the hollow frame 816D. Moreover, the space B between the lens 814B and the lens 814C is connected to the space C inside the hollow frame 816D through the through holes of the lens frame 816C, the through holes 844b of the inner cylinder 844, the groove 842d of the outer cylinder 842, and the through holes of the hollow frame 816D. The space C inside the hollow frame 816D is connected to the inner space 156 of the culture device sub-main body 140 through the opening of the rear end portion of the objective lens 840. Therefore, both of the space A between the lens 814A and the lens 814B and the space B between the lens 814B and the lens 814C are vented to the inner space 156 of the culture device sub-main body 140.

In this manner, in the objective lens 840 of the third embodiment also, in the same manner as the first embodiment, it becomes possible to prevent excessive water vapor from accumulating in the space A between the lens 814A and the lens 814B as well as in the space B between the lens 814B and the lens 814C to cause high humidity. Thus, it becomes possible to prevent dew condensation on the surface of each of the lens 814A, lens 814B, and lens 814C.

In the third embodiment, since the groove 842d of the outer cylinder 842 is formed along the entire circumference of the inner side face, the machining process of the outer cylinder 842 can be carried out comparatively easily.

In the third embodiment, the number of any of the through holes of the lens frame 816B, the through holes of the lens frame 816C, the through holes 844a of the inner cylinder 844, the through holes 844b of the inner cylinder 844, the through holes 844c of the inner cylinder 844, and the through holes of the hollow frame 816D is set to two; however, not limited to this, the number may be changed as appropriate.

Figure 7:
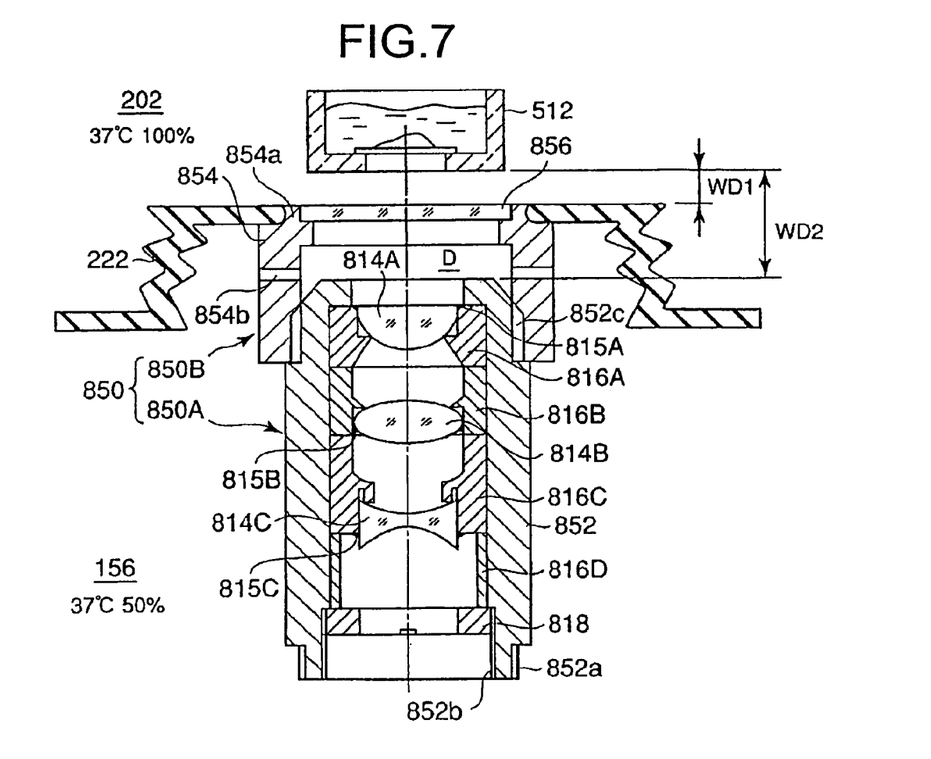
FIG. 7 is a sectional view that shows an objective lens and a peripheral portion thereof in a culture observation apparatus in accordance with a fourth embodiment of the present invention.

A fourth embodiment is directed to another objective lens that is used for the culture observation apparatus and is hardly subjected to dew condensation. FIG. 7 is a sectional view that shows an objective lens and a periphery thereof in a culture observation apparatus in accordance with the fourth embodiment of the present invention. In FIG. 7, those members that are indicated by the same reference numerals shown in FIG. 1 are the same members, and the detailed description thereof is not repeated.

As shown in FIG. 7, an objective lens 850 of the fourth embodiment includes an objective lens main body 850A and a cap 850B that is detachably attached to the objective lens main body 850A.

The objective lens main body 850A is provided with lenses 814A to 814C, lens frames 816A to 816C that hold the lenses 814A to 814C, a hollow frame 816D, an outer cylinder 852 that houses the lens frames 816A to 816C and the hollow frame 816D, and a frame securing member 818 used for securing the lens frames 816A to 816C and the hollow frame 816D.

The outer cylinder 852 has a screw portion 852a at its rear end so as to be attached to the objective lens supporting member 322, and also has a screw portion 852b on an inner circumferential face near its rear end, with which the frame securing member 818 is engaged. Moreover, the outer cylinder 852 has a screw portion 852c at its front end, with which the cap 850B is engaged.

The cap 850B has a cap main body 854 that is held in the objective lens main body 850A and transparent parallel flat plates 856 that are held by the cap main body 854. The cap main body 854 has an engaging portion 854a that is engaged with the sealing member 222. The engaging portion 854a is engaged with the sealing member 222, for example, through fitting. Moreover, the cap main body 854 has a plurality of through holes 854b that extend in diameter directions. Thus, a space D between the parallel flat plates 856 and the lens 814A is vented to the inner space 156 of the culture device sub-main body 140 through the through holes 854b of the cap main body 854.

With this arrangement, it is possible to prevent excessive water vapor from accumulating in the space D between the parallel flat plates 856 and the lens 814A to cause high humidity. Thus, it becomes possible to prevent dew condensation on the surface of each of the lens 814A, lens 814B, and lens 814C.

In the fourth embodiment, the objective lens 850 may be used with the cap 850B being removed, if necessary. More specifically, the cap 850B may be attached only when used under high humidity, and removed when used in the other conditions. By removing the cap 850B, the operational distance is widened from WD1 to WD2. In this case, the possibility that the objective lens main body 850A might collide with the container 512 can be reduced.

Moreover, it is only necessary to screw the cap 850B into the objective lens main body 850A so as to prevent dew condensation; therefore, this structure can be easily added to objective lenses of various kinds by simply forming the screws used for attaching the cap 850 thereto, and generally applied to many objective lenses.

Figure 8:
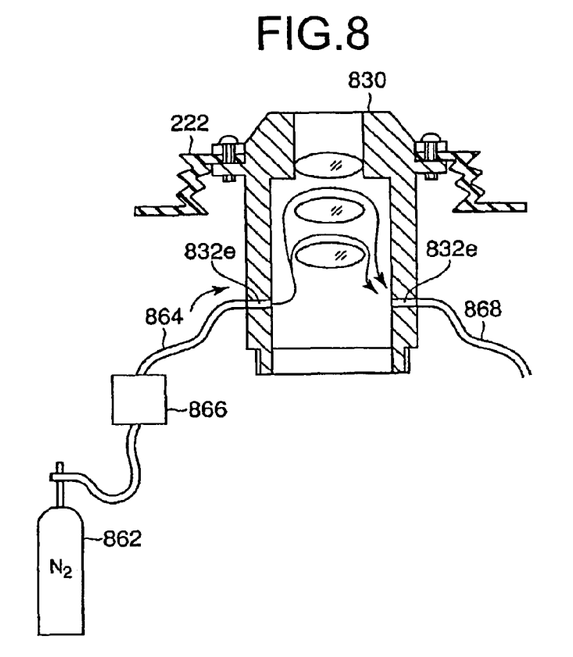
FIG. 8 shows a dry gas circulating device in accordance with a fifth embodiment of the present invention.

In a fifth embodiment, in order to positively prevent the occurrence of dew condensation, a dry-gas circulating device used for circulating a drying gas inside the objective lens 830 is attached to the objective lens 830 shown in FIG. 5. FIG. 8 shows the dry-gas circulating device in accordance with the fifth embodiment of the present invention.

As shown in FIG. 8, the circulating device is provided with a dry-gas supplying unit 862 used for supplying a dry gas, a gas supplying flow path 864 for supplying the dry gas supplied from the dry-gas supplying unit 862 to spaces located among a plurality of lens groups of the objective lens 830, a valve 866 that is placed in the middle of the gas supplying flow path 864, and a gas discharging flow path 868 used for discharging the gas located inside the spaces among the lens groups of the objective lens 830.

The dry-gas supplying unit 862, which is prepared as a gas cylinder, for example, supplies a nitrogen gas (N2), although not particularly limited thereto. Not particularly limited to nitrogen gas (N2), the dry gas may be another appropriate dry gas, such as a carbon dioxide gas (CO2). In the case when CO2 is used, the gas-supplying source 210 (used for the culture space 202) may be used in a shared manner by the use of, for example, a two-way tube.

The gas supplying flow path 864 is connected to one of the through holes 832e of the outer cylinder 832 of the objective lens 830. The gas discharging flow path 868 is connected to the other through hole 832e of the outer cylinder 832 of the objective lens 830, and terminated on the outside of the culture device sub-main body 140. The gas discharging flow path 868 may be terminated in the inner space 156 of the culture device sub-main body 140, and in this case, the gas discharging flow path 868 itself may not be provided.

The dry gas, supplied from the dry-gas supplying unit 862, which has been warmed in the inner space 156 of the culture device sub-main body 140, while passing through the gas supplying flow path 864, is directed into the objective lens 830, and allowed to pass through the space A between the lens 814A and the lens 814B as well as the space B between the lens 814B and the lens 814C, and then discharged through the gas discharging flow path 868. Here, all of the dry-gas supplying unit 862, the valve 866, and the gas supplying flow path 864 may be placed in the inner space 156 so as to be warmed. With this arrangement, since the temperature of the dry gas is made virtually the same as the temperature of the objective lens, it is possible to prevent the focus from deviating due to the dry gas supplied thereto.

In this manner, in the fifth embodiment, since the dry gas is forcefully circulated inside the objective lens 830, the space A between the lens 814A and the lens 814B and the space B between the lens 814B and the lens 814C are maintained in low humidity. Thus, the occurrence of dew condensation inside the objective lens 830 is effectively prevented.

Figure 9:
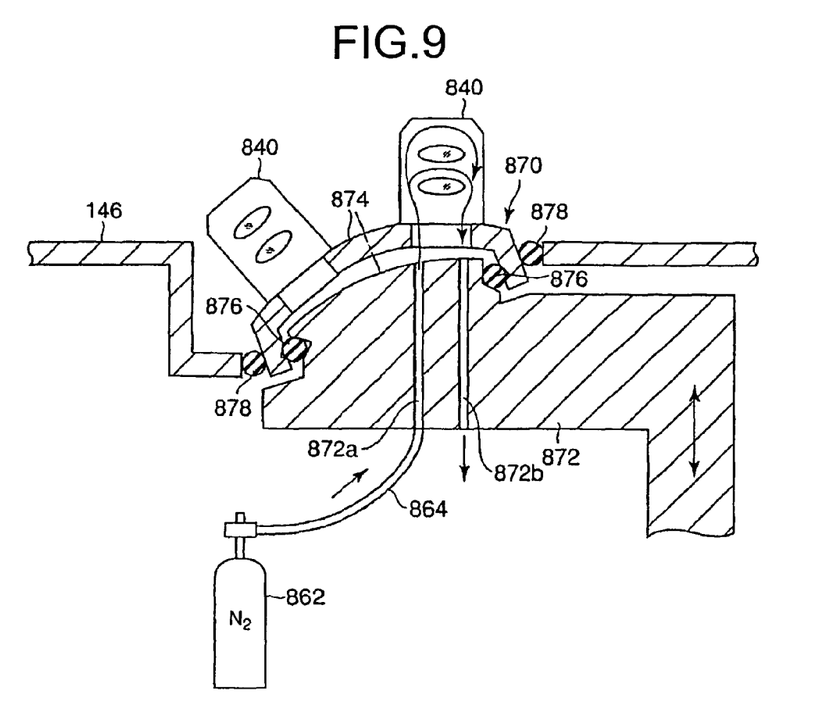
FIG. 9 shows a dry gas circulating device in accordance with a sixth embodiment of the present invention.

In a sixth embodiment, in order to positively prevent the occurrence of dew condensation, a dry-gas circulating device used for circulating or diffusing a drying gas inside the objective lens 840 is attached to the objective lens 840 shown in FIG. 6. FIG. 9 shows the dry-gas circulating device in accordance with the sixth embodiment of the present invention.

As shown in FIG. 9, in place of the objective lens supporting member that supports only one objective lens, an objective optical unit of the sixth embodiment is provided with an objective revolver 870.

The objective revolver 870 is provided with a rotation base 874 to which a plurality of objective lenses 840 can be attached and a supporting unit 872 that rotatably supports the rotation base 874, and one of the objective lenses 840 attached to the rotation base 874 can be selectively placed on the light axis of a microscope. The supporting unit 872 can be longitudinally shifted by the focusing mechanism.

The gap between the supporting unit 872 and the rotation base 874 is sealed by a slidable sealing member 876, and the gap between the rotation base 874 and the upper side base portion 146 is sealed by a slidable sealing member 878. The supporting unit 872 is provided with a through hole 872a used for efficiently supplying a dry gas to the objective lens 840 placed on the light axis of the microscope, and a through hole 872b used for efficiently discharging the dry gas from the objective lens 840 placed on the light axis of the microscope. A gas supplying flow path 864, which is connected to the dry gas supplying unit 862, is connected to the through hole 872a of the supporting unit 872.

The dry gas, supplied from the dry gas supplying unit 862, enters the inside of the objective lens 840 through the gas supplying flow path 864 and the through hole 872a of the supporting unit 872, and is directed through the space A between the lens 814A and the lens 814B as well as the space B between the lens 814B and the lens 814C, and then discharged from the through hole 872a of the supporting unit 872. In the same manner as the sixth embodiment, the through hole 872a for discharging may be either terminated in the inner space 156 of the culture device sub-main body 140 or connected to the outside of the culture device sub-main body 140.

In this manner, since the dry gas is forcefully circulated or diffused inside the objective lens 840, the space A between the lens 814A and the lens 814B and the space B between the lens 814B and the lens 814C are maintained in low humidity. Thus, the occurrence of dew condensation inside the objective lens 840 is effectively prevented.

Figure 10:
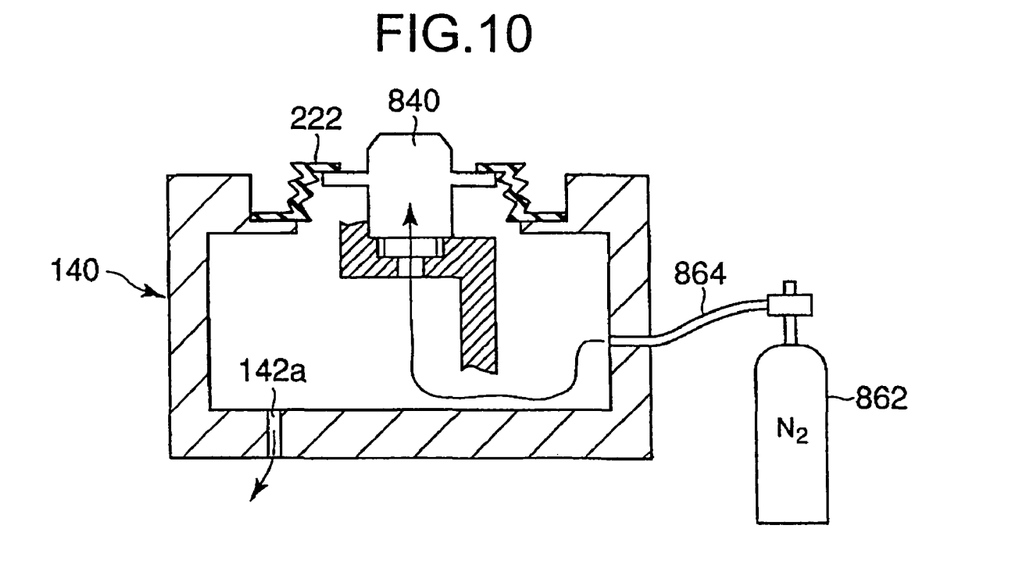
FIG. 10 shows a dry gas circulating device in accordance with a seventh embodiment of the present invention.

A seventh embodiment is directed to another dry-gas circulating device used for circulating or diffusing a drying gas inside the objective lens 840 shown in FIG. 6. FIG. 10 shows the dry-gas circulating device in accordance with the seventh embodiment of the present invention.

As shown in FIG. 10, in the seventh embodiment, the gas supplying flow path 864, connected to the dry-gas supplying unit 862, is connected to the inner space 156 of the culture device sub-main body 140.

The dry gas supplying unit 862 supplies a dry gas to the inner space 156 of the culture device sub-main body 140 through the gas supplying flow path 864. The dry gas, supplied to the inner space 156 of the culture device sub-main body 140, is allowed to enter the inside of the objective lens 840 at a certain substantial possibility, directed through the space A between the lens 814A and the lens 814B as well as the space B between the lens 814B and the-lens 814C, and then discharged through the through hole 142a of the lower base portion 142.

In this manner, since the dry gas is forcefully circulated or diffused inside the objective lens 840, the space A between the lens 814A and the lens 814B and the space B between the lens 814B and the lens 814C are maintained in low humidity. Thus, the occurrence of dew condensation inside the objective lens 840 is effectively prevented.

This arrangement is effectively used in the case when a sufficient space used for installing the dry gas supplying unit 862 is not available inside the culture device sub-main body 140. In this case, since there is no portion in which the dry gas is warmed, a heater or the like, not shown, may be wound around the gas supplying flow path 864 separately so as to carry out a warming process.

Figure 11:
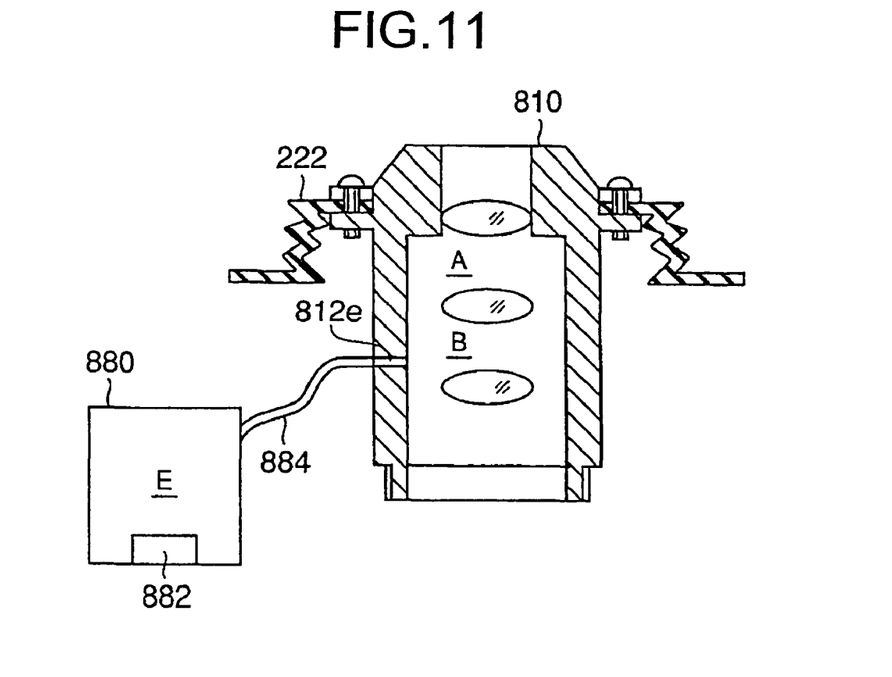
FIG. 11 shows a drying device in accordance with an eighth embodiment of the present invention.

An eighth embodiment is directed to a drying device used for drying the inside of the objective lens. FIG. 11 shows the drying device in accordance with the eighth embodiment of the present invention. FIG. 11 schematically shows a state in which the drying device of the eighth embodiment is applied to the objective lens 810 shown in FIG. 2.

As shown in FIG. 11, the drying device is provided with a desiccant housing unit 880 which houses a desiccant 882 that absorbs moisture and a communicating flow path 884 which allows the inner space of the desiccant housing unit 880 to communicate with spaces among a plurality of lens groups of the objective lens 810.

Although not particularly limited, the desiccant 882 is made of, for example, silica gel. The communicating flow path 884 has one end connected to the desiccant housing unit 880, and the other end connected to the through hole 812e of the outer cylinder 812 of the objective lens 810.

Moisture located inside the objective lens 840 is absorbed by the desiccant 882 inside the desiccant housing unit 880 through the communicating path 884. For this reason, the space A between the lens 814A and the lens 814B and the space B between the lens 814B and the lens 814C are maintained in a low-moisture state. Thus, the occurrence of dew condensation inside the objective lens 840 is effectively prevented.

Figure 12:
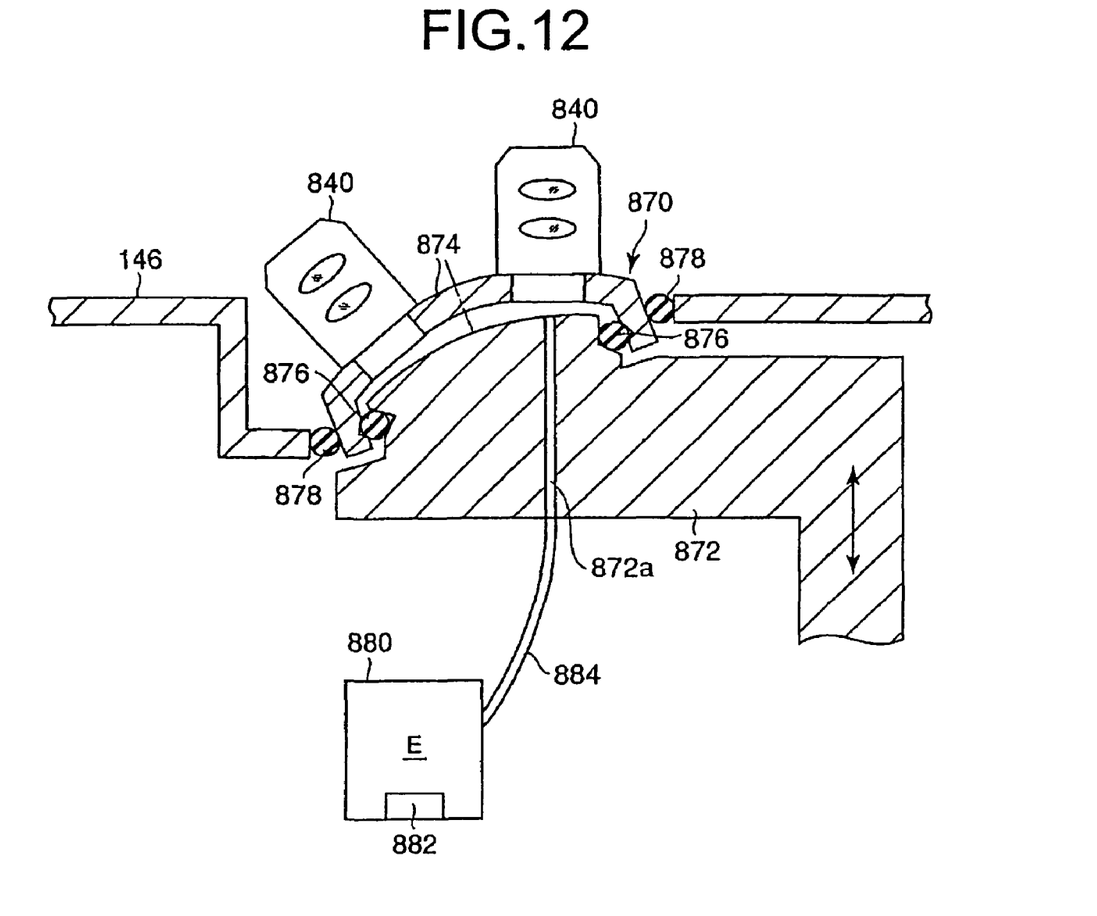
FIG. 12 shows a drying device in accordance with a modification of the eighth embodiment of the present invention.

FIG. 12 shows a drying device in accordance with a modification of the eighth embodiment of the present invention. FIG. 12 schematically shows a state in which the drying device in accordance with the modification is applied to the objective lens 840 shown in FIG. 6.

As shown in FIG. 12, in the present modification, the objective lens 840 is attached to the objective revolver 870. The objective revolver 870 and the structures on the periphery thereof are virtually the same as those shown in FIG. 9. Here, the supporting unit 872 is provided with only one through hole 872a that communicates with the inner space of the objective lens 840 attached to the rotation base 874. The communicating flow path 884 has one end connected to the desiccant housing unit 880, and the other end connected to the through hole 872a of the supporting unit 872.

Moisture located inside the objective lens 840 is absorbed by the desiccant 882 inside the desiccant housing unit 880 through the through hole 872a of the supporting unit 872 and the communicating path 884. For this reason, the space A between the lens 814A and the lens 814B and the space B between the lens 814B and the lens 814C are maintained in a low-moisture state. Thus, the occurrence of dew condensation inside the objective lens 840 is effectively prevented.

In the present modification, since no fast flow of a gas is generated, neither temperature changes nor dust adhesion to the lens due to scattered dusts are caused by a flow of a gas.

Here, it is not possible to place a large amount of silica gel or the like inside the objective lens and the narrow spaces in the objective lens; however, since the desiccant housing unit 880 is externally installed, it becomes possible to ensure a larger space and also to put a large amount of silica gel so that dew condensation can be prevented for a long time. Moreover, since only the space inside the objective lens that is most susceptible to dew condensation is dried, the silica gel consumption can be reduced to the minimum amount required.

Figure 13:
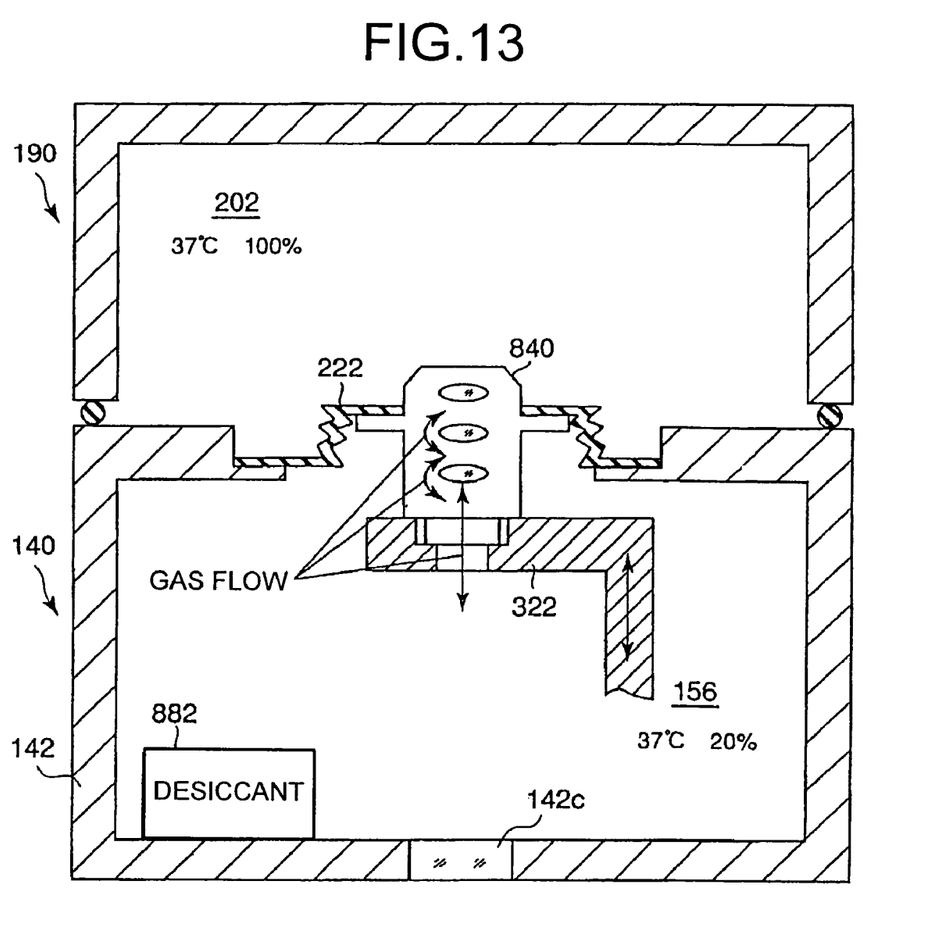
FIG. 13 schematically shows a culture observation apparatus in accordance with a ninth embodiment of the present invention.

A ninth embodiment is directed to a culture observation apparatus that is provided with a drying means used for drying the inside of the objective lens. FIG. 13 schematically shows the culture observation apparatus in accordance with the ninth embodiment of the present invention.

In the culture observation apparatus shown in FIG. 13, although not particularly limited to this structure, for example, the objective lens 840 shown in FIG. 6 is attached to the objective lens supporting member 322. However, the objective lens to be attached to the objective lens supporting member 322 is not intended to be limited to the objective lens 840, and may be altered to any of the objective lens 810, the objective lens 820, the objective lens 830, and the objective lens 850 that have been discussed above, without causing any problems.

In the ninth embodiment, no through hole that connects the inner space 156 of the culture device sub-main body 140 to the outside space is formed in the lower-side base portion 142 of the culture device sub-main body 140, and as shown in FIG. 13, a desiccant 882 is placed as the drying means inside the inner space 156 of the culture device sub-main body 140.

Since moisture located in the inner space 156 of the culture device sub-main body 140 is absorbed by the desiccant 882, the inner space 156 of the culture device sub-main body 140 is maintained in a low-moisture state. For this reason, the space A between the lens 814A and the lens 814B and the space B between the lens 814B and the lens 814C are maintained in a low-moisture state. Thus, the occurrence of dew condensation inside the objective lens 840 is effectively prevented. Moreover, the occurrence of dew condensation on the optical window 142c attached to the lower base portion 142 is also prevented.

Since the inner space 156 of the culture device sub-main body 140 is comparatively large, it is possible to put a large amount of the desiccant 882 therein at one time. Therefore, by placing a large amount of the desiccant 882 in the inner space 156 of the culture device sub-main body 140, it becomes possible to prevent the occurrence of dew condensation for a long time.

In the ninth embodiment also, since no fast flow of a gas is generated, neither temperature changes nor dust adhesion to the lens due to scattered dusts are caused by a flow of a gas.

Moreover, since the inner space 156 does not ventilate the outside air, the inner space 156 is easily maintained at a constant temperature.

Figure 14:
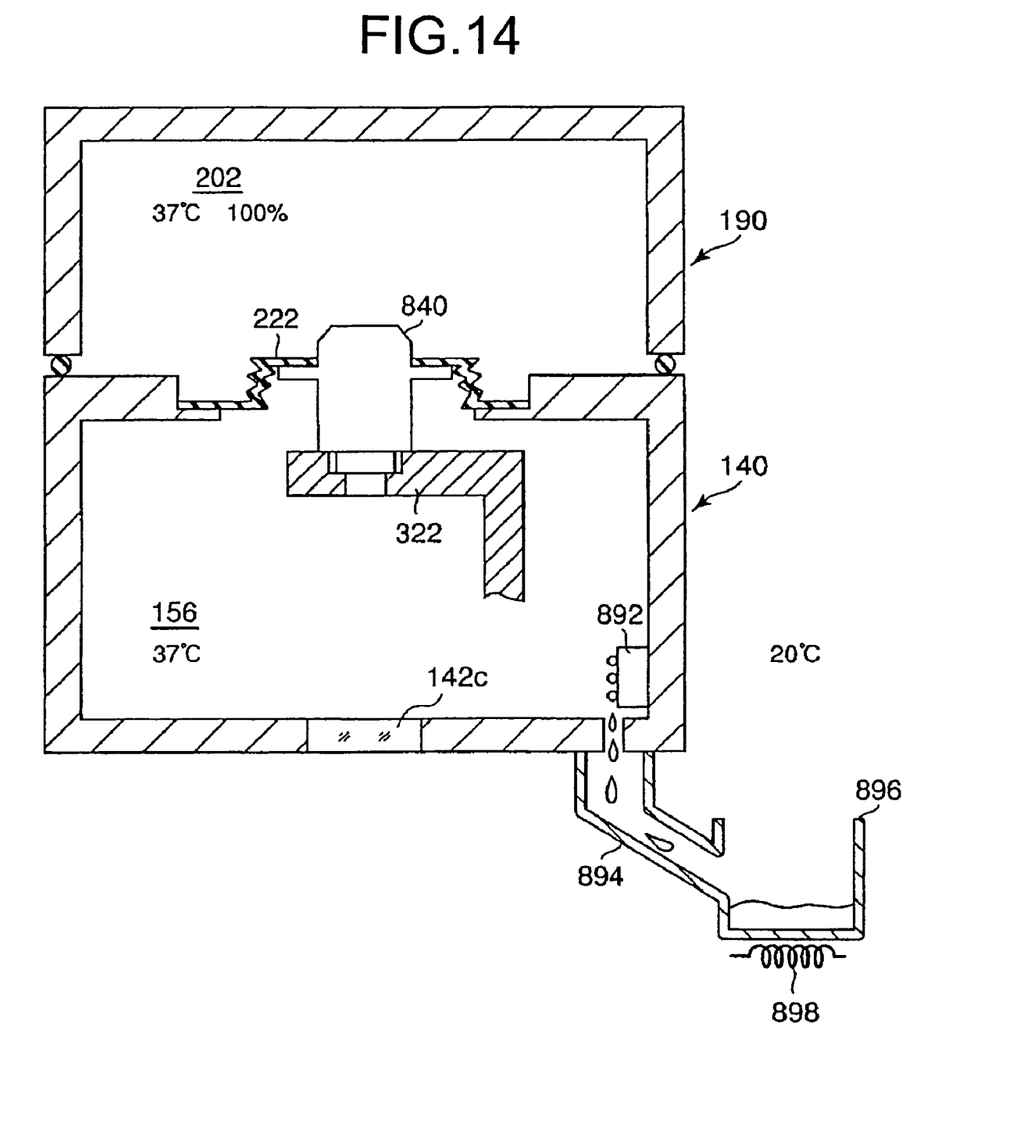
FIG. 14 schematically shows a culture observation apparatus in accordance with a tenth embodiment of the present invention.

A tenth embodiment is directed to a culture observation apparatus that is provided with another drying means used for drying the inside of the objective lens. FIG. 14 schematically shows the culture observation apparatus in accordance with the tenth embodiment of the present invention.

In the culture observation apparatus shown in FIG. 14, although not particularly limited to this structure, for example, the objective lens 840 shown in FIG. 6 is attached to the objective lens supporting member 322. However, the objective lens to be attached to the objective lens supporting member 322 is not intended to be limited to the objective lens 840, and may be altered to any of the objective lens 810, the objective lens 820, the objective lens 830, and the objective lens 850 that have been discussed above, without causing any problems.

In the culture observation apparatus of the tenth embodiment, the culture device sub-main body 140 is provided with a liquefying device 892 that changes moisture in the inner space 156 into liquid, a discharging flow path 894 used for externally discharging the resulting liquid in the liquefying device 892, a liquid storing unit 896 for storing the liquid discharged through the discharging flow path 894, and a vaporizer 898 for vaporizing the accumulated liquid in the liquid storing unit 896. Not particularly limited to this structure, the liquefying device 892 may be formed by a Peltier element. Not particularly limited to this structure, the vaporizer 898 may be formed by a heater.

In the tenth embodiment, moisture located in the inner space 156 of the culture device sub-main body 140 is changed into water droplets by the liquefying device 892, and the water droplets are accumulated in the liquid storing unit 896 through the discharging flow path 894. The water accumulated in the liquid storing unit 896 is vaporized by the vaporizer 898.

With this arrangement, the inner space 156 of the culture device sub-main body 140 is maintained in a low-moisture state. Therefore, the space A between the lens 814A and the lens 814B and the space B between the lens 814B and the lens 814C are maintained in a low-moisture state. Thus, the occurrence of dew condensation inside the objective lens 840 is effectively prevented. Moreover, the occurrence of dew condensation on the optical window 142c attached to the lower base portion 142 is also prevented.

The following effects are also obtained. Since no fast flow of a gas is generated, neither focus deviations due to temperature changes nor image degradation due to dust adhesion to the lens resulting from scattered dusts are caused. Moreover, different from a drying gas and silica gel, nothing is consumed so that no exchanging operations are required. Furthermore, since a high moisture-absorbing performance is provided, it becomes possible to positively prevent dew condensation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A culture observation apparatus, which is used for observing a cultured cell while culturing the cell, comprising:
   a culture device that cultures the cultured cell, the culture device including a first space that is controlled to an environment suitable for culture of the cell, and a second space that is controlled to a lower humidity condition than the first space; and
   a microscope which is used for observing the cultured cell, and which includes an objective optical unit including an objective lens;
   wherein the objective lens comprises a plurality of lenses, a plurality of lens frames that hold the lenses and that have at least one through hole, and a cylinder member that houses the lens frames to be held therein;
   wherein the cylinder member extends into the first space through an opening formed in a partition wall that separates the first space and the second space, with a gap between the cylinder member and the partition wall being sealed by a sealing member;
   wherein a first part of the cylinder member is exposed in the first space and a second part of the cylinder member is exposed in the second space;
   wherein the objective lens includes a flow path which makes a space formed by the lenses and the lens frames to be vented with the second space; and
   wherein the cylinder member has a flow path that connects the through hole of the lens frames to the second space.

2. The culture observation apparatus according to claim 1, wherein the flow path of the cylinder member extends through the cylinder member.

3. The culture observation apparatus according to claim 1, wherein the flow path of the cylinder member extends toward a rear end of the cylinder member.

4. The culture observation apparatus according to claim 1, further comprising a circulating device that circulates or diffuses a dry gas in the space formed by the lenses and the lens frames.

5. The culture observation apparatus according to claim 4, wherein the circulating device includes:
   a dry gas supplying unit, and
   a supplying flow path used for supplying the dry gas supplied from the dry gas supplying unit to the space formed by the lenses and the lens frames.

6. The culture observation apparatus according to claim 5, wherein:
   at least one of the plurality of lens frames has a through hole; and
   the cylinder member has at least two flow paths that connect the through holes of the lens frames to the second space, with the supplying flow path of the circulating device being connected to one of the flow paths of the cylinder member.

7. The culture observation apparatus according to claim 6, wherein the flow path of the cylinder member extends through the cylinder member.

8. The culture observation apparatus according to claim 6, wherein:
   the flow path of the cylinder member extends toward a rear end of the cylinder member;
   the objective optical unit has an objective lens supporting member that supports the objective lens; and
   the supplying flow path of the circulating device extends in a manner so as to penetrate the objective lens supporting member.

9. The culture observation apparatus according to claim 5, wherein the supplying flow path of the circulating device is connected to the second space of the culture device.

10. The culture observation apparatus according to claim 1, further comprising a drying unit used for removing moisture in the space formed by the lenses and the lens frames.

11. The culture observation apparatus according to claim 10, wherein the drying unit includes:
    a desiccant housing unit that houses a desiccant for absorbing moisture, and
    a communicating flow path that allows an inner space of the desiccant housing unit to communicate with the space formed by the lenses and the lens frames.

12. The culture observation apparatus according to claim 11, wherein:
    at least one of the plurality of lens frames has a through hole;
    the cylinder member has a flow path that connects the through hole of the lens frame to the second space; and
    the communicating flow path of the drying unit is connected to the flow path of the cylinder member.

13. The culture observation apparatus according to claim 12, wherein the flow path of the cylinder member extends through the cylinder member.

14. The culture observation apparatus according to claim 12, wherein:
    the flow path of the cylinder member extends toward a rear end of the cylinder member;
    the objective optical unit has an objective lens supporting member that supports the objective lens; and
    the communicating flow path of the drying unit extends in a manner so as to penetrate the objective lens supporting member.

15. The culture observation apparatus according to claim 10, wherein the drying unit comprises a desiccant that is put in the second space of the culture device.

16. The culture observation apparatus according to claim 10, wherein the drying unit includes:
    a liquefying unit that changes moisture inside the second space of the culture device into a liquid, and
    a discharging flow path used for discharging the liquid generated in the liquefying unit out of the second space.

17. A culture observation apparatus, which is used for observing a cultured cell while culturing the cell, comprising:
    a first space that is controlled to an environment suitable for culture of the cell;
    a second space that is controlled to a lower humidity condition than the first space, for observation of the cultured cell;
    a partition wall that separates the first space and the second space;
    an objective optical unit including an objective lens for observation of the cultured cell, wherein the objective lens is held in the second space and extends into the first space through an opening formed in the partition wall, and wherein the objective lens includes a plurality of lenses, a plurality of lens frames that hold the lenses, and a cylinder member that houses the lens frames to be held therein;
    a sealing member that seals a gap between the cylinder member and the partition wall; and
    a flow path that makes a space formed by the lenses and the lens frames to be vented with the second space so as to prevent dew condensation on the surface of the objective lens and inside of the objective lens;

wherein a first part of the cylinder member is exposed in the first space and a second part of the cylinder member is exposed in the second space.

18. A culture observation apparatus, which is used for observing a cultured cell while culturing the cell, comprising:

a first space that is controlled to an environment suitable for culture of the cell;

a second space that is controlled to a lower humidity condition than the first space, for observation of the cultured cell;

a partition wall that separates the first space and the second space;

an objective optical unit that is held in the second space and extends into the first space through an opening formed in the partition wall, the objective optical unit including an objective lens for observation of the cultured cell, wherein the objective lens includes a plurality of lenses, a plurality of lens frames that hold the lenses, and a cylinder member that houses the lens frames to be held therein;

a cap that is detachably attached to an outer face of the cylinder member at a front end of the objective lens;

at least one transparent, parallel flat plate that is held by the cap and arranged between the cultured cell and the objective lens;

a sealing member that seals a gap between the cap and the partition wall; and a through hole that is provided in the cap and that communicates a space between the cap and the cylinder member of the objective lens with the second space so as to prevent dew condensation on the surface of the objective lens and inside of the objective lens.

* * * * *